United States Patent [19]

Suzuki et al.

[11] Patent Number: 5,592,098

[45] Date of Patent: Jan. 7, 1997

[54] CHANNEL FORMING FUEL PERMITTIVITY SENSOR WITH AUTOMATIC TEMPERATURE COMPENSATION

[75] Inventors: Hiroyoshi Suzuki; Akira Okada; Takahiro Moronaga, all of Hyogo, Japan

[73] Assignee: Mitsubishi Denki Kabushiki Kaisha, Tokyo, Japan

[21] Appl. No.: 487,515

[22] Filed: Jun. 7, 1995

Related U.S. Application Data

[62] Division of Ser. No. 279,550, Jul. 25, 1994, which is a continuation of Ser. No. 935,210, Aug. 26, 1992, abandoned.

[30] Foreign Application Priority Data

| Aug. 28, 1991 | [JP] | Japan | 3-216825 |
| Aug. 28, 1991 | [JP] | Japan | 3-216840 |
| Sep. 12, 1991 | [JP] | Japan | 3-232863 |

[51] Int. Cl.$^6$ ............................ G01N 27/22; G01R 27/26
[52] U.S. Cl. .......................... 324/663; 324/675; 324/682; 73/61.43
[58] Field of Search ..................... 324/663, 674, 324/675, 681, 682, 685, 686; 73/61.43

[56] References Cited

U.S. PATENT DOCUMENTS

| 4,187,462 | 2/1980 | Haker et al. | 324/655 |
| 4,905,655 | 3/1990 | Maekawa | 123/494 |
| 4,939,468 | 7/1990 | Takeuchi | 324/690 |
| 5,005,402 | 4/1991 | Pischinger et al. | 73/61.10 R |
| 5,103,184 | 4/1992 | Kapsokavathis et al. | 324/663 X |
| 5,124,654 | 6/1992 | Scheid | 324/663 X |
| 5,150,683 | 9/1992 | Depa et al. | 123/494 X |
| 5,255,656 | 10/1993 | Rader et al. | 123/494 |
| 5,313,168 | 5/1994 | Ogawa | 324/663 |
| 5,337,017 | 8/1994 | Ogawa | 324/682 |
| 5,414,367 | 5/1995 | Ogawa | 324/663 |
| 5,414,368 | 5/1995 | Ogawa et al. | 324/675 |
| 5,418,465 | 5/1995 | Seipler et al. | 324/663 |

FOREIGN PATENT DOCUMENTS

| 62-25248 | 2/1987 | Japan . |
| 63-31734 | 6/1988 | Japan . |
| 2-41155 | 3/1990 | Japan . |

OTHER PUBLICATIONS

Pinnock, "A Petrol/Alcohol Ratio Sensor for Flexible–Fuel Vehicles", May, 1992, IEEE Colloquim on Automotive Sensor (Dic 107) pp. 4/1–4/3.

Takeuchi et al., "A Capacitance Sensor for Methanol Ratio Measurement of Blended Gasoline", OCt. 1991, IEE, pp. 24–28.

Primary Examiner—Kenneth A. Wieder
Assistant Examiner—Glenn W. Brown
Attorney, Agent, or Firm—Sughrue, Mion, Zinn, Macpeak & Seas

[57] ABSTRACT

A tubular single-layer winding coil is installed on the outer periphery of a thin wall portion of a cylindrical container case and a columnar electrode is provided at the center of the inside of the cylindrical container case. A fuel channel is formed between the coil and the electrode so that the permittivity of fuel flowing through the fuel channel is detected from the electrostatic capacity therebetween. Further, variation of the electrostatic capacity due to the temperature characteristics of the fuel is compensated by the temperature characteristics of the permittivity of the thin wall portion of the sensor unit. Furthermore, variation of the electrostatic capacity due to the temperature characteristics of the fuel is compensated by the temperature compensation capacitor which is connected with the single layer winding coil in parallel.

10 Claims, 13 Drawing Sheets

MOLD 1

CHANNEL FORMING FUEL PERMITTIVITY SENSOR WITH AUTOMATIC TEMPERATURE COMPENSATION

This is a divisional of application Ser. No. 08/279,550 filed Jul. 25, 1994, which is a continuation of application Ser. No. 07/935,210, filed Aug. 26, 1992, now abandoned.

BACKGROUND OF THE INVENTION

The present invention relates to an apparatus for detecting the permittivity of fuel supplied to a combustion chamber in a non-contact way to determine the properties of the fuel, and more particularly to an apparatus for measuring the alcohol content of alcohol-mixed fuel for use in automotive engines.

Fuel prepared by mixing alcohol with gasoline is being increasingly introduced for use in automobiles in order to reduce not only oil consumption but also atmospheric pollution due to automotive exhaust gas. However, the direct use of such alcohol-mixed fuel for engines designed to match with the air/fuel ratio of gasoline has made driving difficult because the theoretical air/fuel ratio of alcohol is lower than that of gasoline, that is, the air/fuel ratio of the former is leaned. Therefore, it has been customary to detect the alcohol content of alcohol-mixed fuel so as to regulate the air/fuel ratio, ignition timing and the like in accordance with the value detected.

In order to detect the percentage of alcohol, there have heretofore been proposed systems of utilizing the variation of electrostatic capacity to detect the permittivity of alcohol-mixed fuel. Among those of the sort stated above, Unexamined Japanese Patent Publication (Kokai) Sho-62-25248 (1987) and Post Examined Japanese Patent Publication (Kokoku) Sho-63-31734 (1988) disclose systems in which a coil is installed close to a fuel channel so that the permittivity of fuel is detected by utilizing the variation of floating capacity between the coil and another coil adjacent to the former or that of electrostatic capacity between the coil and an electrode adjacent thereto. Referring to FIGS. 1 to 3, such a system will be described.

FIG. 1 shows the construction of a conventional fuel permittivity detecting sensor, wherein numeral 1 denotes an insulating tube made of ceramic, oil-resistant plastic material or the like having a fuel passageway 4 inside, 16 an excitation electrode wound in a ring-like form on part of the outer periphery of the insulating tube 1, and 3 a single-layer winding coil also wound on the insulating tube 1 apart by a predetermined distance from the excitation electrode 16, these forming a sensor unit A. Further, reference B denotes a detection circuit connected to the sensor unit A and the following arrangement is made therein: the output of a sawtooth wave oscillation circuit 21 is connected to a voltage controlled oscillation circuit 22; the output of the voltage control oscillation circuit 22 is connected to the excitation electrode 16; one end of the single-layer winding coil 3 is grounded, this end being located opposite to the excitation electrode 16; a signal on the other end side of the single-layer winding coil 3 is connected via a full-wave rectifying circuit 23 to a peak detector 24; the output of the peak detector 24 is input to a sample hold circuit 25 to which the output of the sawtooth wave oscillation circuit 21 is input; and the output of the sample hold circuit 25 is output via a low-pass filter 26. FIG. 2A is a sectional diagram of the sensor unit A. FIG. 2B is a equivalent circuit diagram for the sensor unit. FIG. 3 is a graph showing the output characteristic of the sensor unit.

The operation of the aforementioned conventional sensor will subsequently be described. The frequency of the signal applied from the voltage control oscillation circuit 22 to the excitation electrode 16 is so controlled that it is swept by the output of the sawtooth wave oscillation circuit 21. If the permittivity $\epsilon$ of fuel is different from what is intended then, the induced voltage in the single-layer winding coil 3 will indicate a maximum value with a different frequency. This is because an electrostatic capacity Cf corresponding to the permittivity $\epsilon$ of the fuel within the fuel passageway 4 between the excitation electrode 16 and the single-layer winding coil 3 together with the self-inductance L of the single-layer winding coil 3 causes LC resonance, whereby the induced voltage of the single-layer winding coil 3 is maximized by the resonance frequency.

As shown in FIG. 2B, the series resonance frequency $f_0$ of the equivalent circuit of the sensor unit is roughly expressed by $$f_0 = 1/[2\pi\sqrt{L\sqrt{\{Cf/(1+Cf/Cs)+Cp+Cpa\}}}] \tag{1}$$

where L=self-inductance of the single-layer winding coil 3; Cf=capacity within the fuel channel 4 between the excitation electrode 16 and the single-layer winding coil 3, the capacity corresponding to permittivity $\epsilon$; Cs=capacity of the tube wall of the insulating tube 1; Cp=capacity in the axial direction of the insulating tube 1 between the electrode 16 and the coil 3; Cpa=external floating capacity between the electrode 16 and the coil 3; and Cpc=floating capacity existing in parallel to the coil 3.

The resonance frequency $f_0$ decreases as capacity Cf increase, that is, the permittivity $\epsilon$ of fuel increases as shown in Eq. (1). The induced voltage of the coil 3 is converted into a d.c. signal in the full-wave rectifying circuit 23 and its maximum value is detected by the peak detector 24. Further a peak detection pulse is supplied to the sample hold circuit 25 and the sweep output of the sawtooth wave oscillation circuit 21 is held for sampling. Therefore, the holding voltage at this time becomes equivalent to the resonance frequency $f_0$ and the voltage output is output outside via the low-pass filter 26 as Vout.

The following problems inevitably arise as the electrode 16 is coaxially arranged on the edge face of the coil in the aforementioned conventional sensor. For instance, given L=20 μH; the outer diameter $\phi$ of the insulating tube 1=10 mm; the wall thickness t of the insulating tube 1=1 mm; and the distance d between the edge face of the coil 3 and that of the electrode 16=2 mm, large parallel capacities Cp, Cpa with respect to the capacity Cf varying with the permittivity $\epsilon$ of fuel exist when the fuel is a mixture of gasoline of $\epsilon$=2 and methanol of $\epsilon$=33 and since their resonance frequencies $f_0$ equally become about 8 MHz, the difference therebetween only remains at about 5% as shown in FIG. 3.

Due to the distance d between the edge faces of the coil and the electrode, moreover, there arise some problems including the difficulty of securing precision, the wide variation of resonance frequency $f_0$ depending on the surface condition changing with the dirt in the insulating tube 1, the external moisture or the like, and these worsen output reproducibility. If, the distance d is increased to secure precision, the capacity Cf also decreases, though the capacities Cp, Cpa are reduced and the permittivity of $f_0$, far from abating, tends to decrease while the resonance frequency $f_0$ only increase on the average. In other words, it is not possible to secure a high output changing ratio relative to the change of the permittivity $\epsilon$ in the conventional sensor and a great sensor-to-sensor output variation causes the sensor output to be easily affected by the external condition. The problem is that the sensor precision is poor.

There arises a further problem in that since the permittivity of fuel has temperature characteristics, the resonance frequency tends to vary, depending on the temperature measured even though the fuel has the same concentration.

A temperature compensation method is generally implemented by providing a thermistor within a fuel channel and connecting the thermistor to a temperature compensation circuit. However, such an arrangement not only increases the size of the apparatus but also makes it costly because a new circuit is additionally installed.

SUMMARY OF THE INVENTION

The present invention has been made to solve the foregoing problems and it is therefore an object of the invention to provide an apparatus for detecting the permittivity of fuel with precision and such an apparatus as is capable of not only increasing output variation relative to the variation of permittivity $\epsilon$ but also making output variations and external conditions less affect the detecting operation.

It is another object of the present invention to provide an apparatus for detecting the permittivity of fuel by detecting the percentage of methanol in the fuel with precision, using the temperature characteristics of the permittivity of an insulating material or a temperature compensation capacitor which is connected in parallel with a coil to compensate for the temperature characteristics of the permittivity of the fuel.

An apparatus for detecting the permittivity of fuel according to the present invention comprises a tubular or planar single-layer winding coil having a thin, high-permittivity insulating wall in hermetical contact with the peripheral or planar face on the side in contact with the fuel, a metal electrode for forming a fuel channel opposite to and with the coil, and a means for detecting the permittivity of the fuel from the electrostatic capacity between the coil and the electrode.

According to the present invention, fuel is made to flow through the fuel channel formed between the single-layer winding coil and the metal electrode, whereby the permittivity of the fuel is detected from the electrostatic capacity between the coil and the electrode.

The apparatus for detecting the permittivity of fuel according to the present invention is capable of detecting the permittivity of fuel with high accuracy by compensating the temperature characteristics of the permittivity of the fuel according to the temperature characteristics of the permittivity of the insulating thin wall portion.

In the apparatus for detecting the permittivity of fuel according to the present invention, a temperature compensating capacitor is provided at a position where the temperature characteristics of the fuel are detectable. The temperature compensating capacitor is connected to the single layer winding coil in parallel so as to offset the temperature characteristics of the resonance variation due to the temperature characteristics of the permittivity of the fuel by means of the temperature compensating capacitor. Thereby, the permittivity of fuel is detected in all time with high accuracy, irrespective of the variation of temperature in the apparatus.

DESCRIPTION OF THE PREFERRED EMBODIMENTS

Embodiment 1

Figure 3:
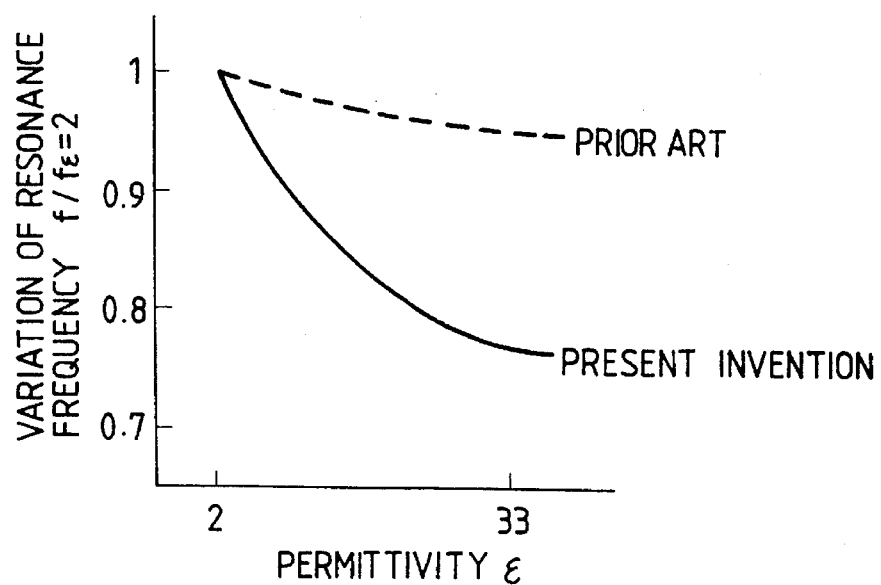
FIG. 3 is a graph showing output characteristics of the conventional sensor and what embodies the present invention.
Figure 4A:
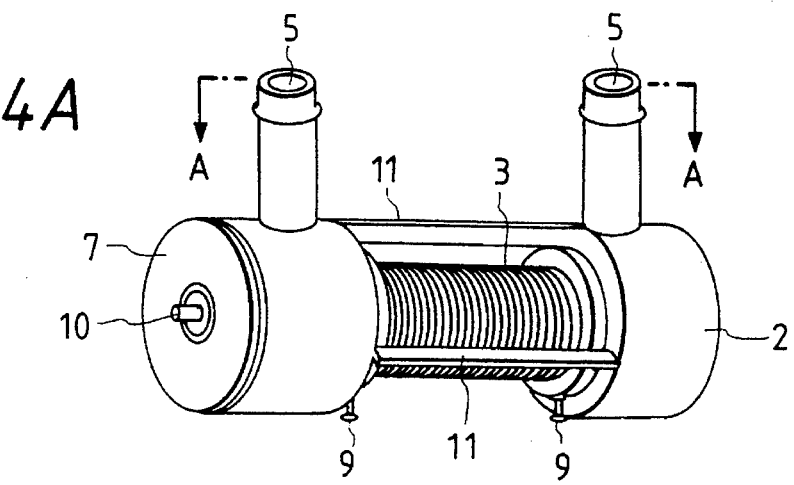
FIGS. 4A and 4B are a perspective view of a sensor unit in a first embodiment of the present invention and a sectional view of the sensor unit.

Referring to the accompanying drawings, embodiments of the present invention will subsequently be described. FIG. 4A is a perspective view of a permittivity detecting sensor in a first embodiment of the present invention and FIG. 4B a sectional view taken on line A—A of FIG. 4A. FIGS. 5A and 5B are diagrams illustrating an equivalent circuit of the sensor. FIG. 3 is a graph showing output characteristics.

Figure 4B:
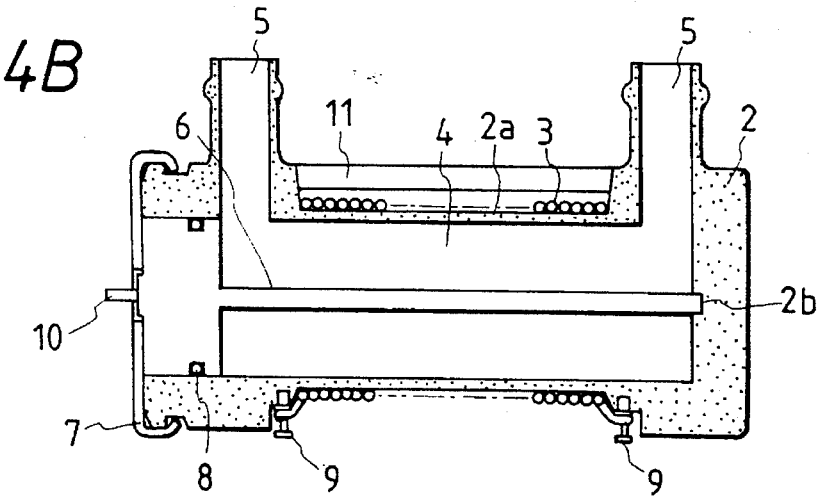
Figure 5A:
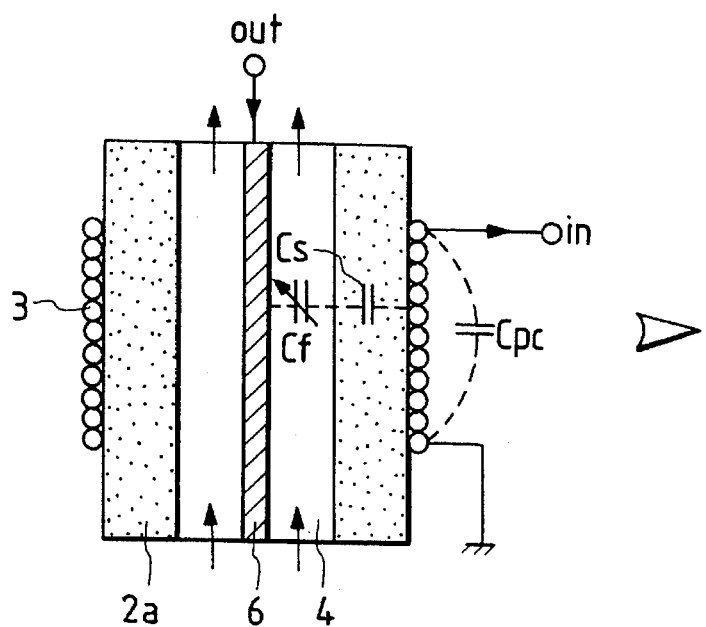
FIGS. 5A and 5B are a block diagram of an equivalent circuit of the sensor unit and an equivalent circuit diagram in the first embodiment of the present invention.
Figure 5B:
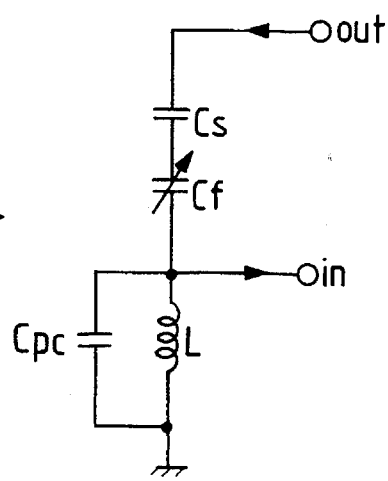

In FIGS. 4A and 4B, numeral 2 denotes a cylindrical container case formed of plastic insulating material, the cylindrical case having a thin wall portion 2a in the center. Relatively high dielectric oil resistant epoxy resin, PPS resin or the like may preferably be used as the plastic material to improve the output changing ratio and the properties resistant against fuel. However, PPS resin is especially preferred in that it can be used for injection molding. Numeral 3 denotes a cylindrical single-layer coil wound on the outer periphery of the thin wall portion 2a of the case 2; 4, a fuel channel formed in the case 2; 5, a pair of fuel ports provided at the respective ends of the fuel channel 4; and 6, a columnar electrode which is coaxial with and opposite to the inner peripheral face of the coil 3. The columnar electrode may be made of stainless or titanium, or otherwise copper, brass, iron or the like covered with nickel so as to increase resistance against fuel.

It is advantageous in view of improving the output changing ratio of the sensor in this case to set the diameter of the columnar electrode 6 smaller than the inner diameter of the thin wall portion 2a on which the coil 3 is wound. An O-ring 8 is fitted to one end of the columnar electrode 6 in such a way that it is in agreement with the inner diameter of the case 2, whereas the other end thereof is fitted into a recess 2b provided in the case 2. The fuel is thus sealed up. A metal fitting 7 is secured to the case 2 by caulking to secure one end of the columnar electrode 6 to the case 2. Numeral 9 denotes a pair of coils fitted to the case 2 by inserting, the respective ends of the coil 3 being soldered thereto; 10, an electrode terminal formed in such a way that part of the columnar electrode 6 is projected outside through the central hole of the metal fitting 7; and 11, a reinforcing beam provided on the outer periphery of the thin wall portion 2a to reinforce the strength of the case 2.

Figure 1:
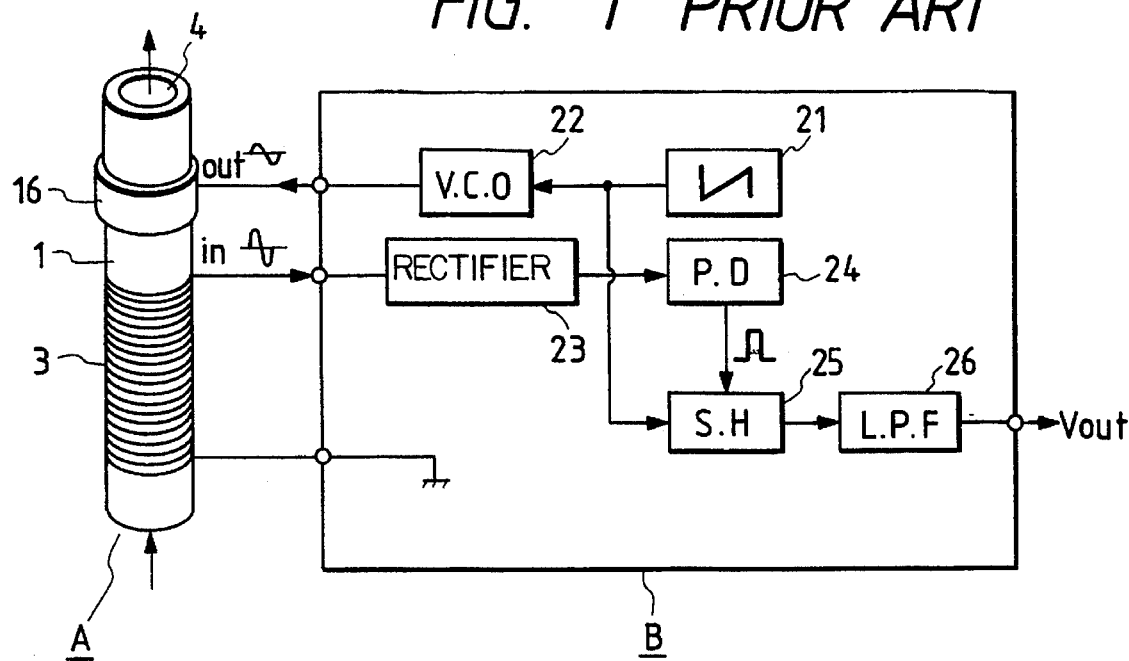
FIG. 1 is a block diagram of a conventional sensor.
Figure 2A:
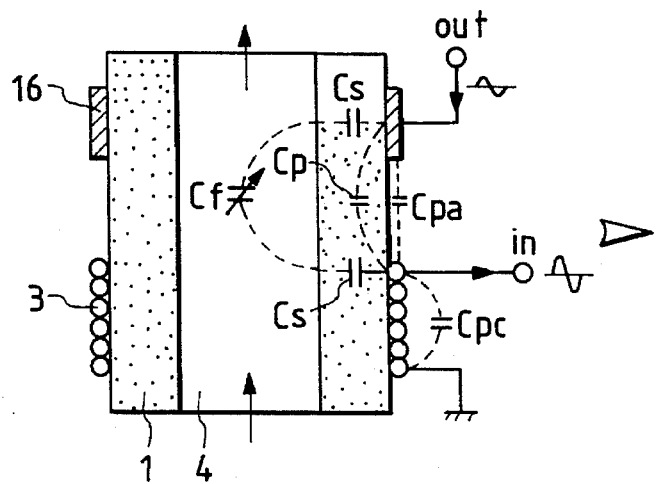
FIGS. 2A and 2B are a block diagram of an equivalent circuit in a sensor unit of the conventional sensor and an equivalent circuit diagram therein.
Figure 2B:
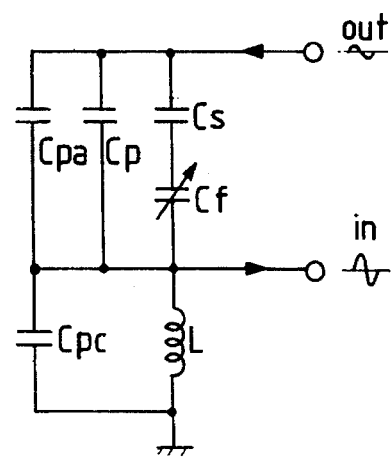

The operation of the sensor will subsequently be described. A detection circuit B of the sensor is similar to what is shown in FIG. 1, wherein the output of a voltage control oscillation circuit 22 is connected to the electrode terminal 10 of the columnar electrode 6 and one coil terminal 9 of the coil 3 is grounded, whereas the other coil terminal 9 is connected to a full-wave rectifying circuit 23. Unlike the prior art, either coil terminal 9 may be grounded.

FIGS. 5A and 5B illustrate an equivalent circuit of the sensor thus connected, wherein Cf represents an electrostatic capacity at the time fuel flows through the fuel channel 4 between the outer periphery of the columnar electrode 6 and the inner periphery of the thin wall portion 2a at a permittivity $\epsilon$, Cs an electrostatic capacity in the thickness direction of the thin wall portion 2a, Cpc a floating capacity existing in parallel to the coil 3 as in the prior art, and Cf what forms as before a series resonance circuit with the self-inductance L of the coil 3, its resonance frequency fm being given by $$fm = \frac{1}{2\pi \sqrt{L} \sqrt{\frac{Cf}{(1 + Cf/Cs)}}} \quad (2)$$

The resonance frequency fm decreases as the permittivity $\epsilon$ of the fuel increases.

Accordingly, the voltage output Vout is made to correspond in value to the resonance frequency fm of the sensor, that is, the permittivity $\epsilon$ of the fuel through the steps of causing the voltage control oscillation circuit 22 to vary the frequency to be applied to the columnar electrode 6, causing the full-wave rectifying circuit 23 to rectify the induced voltage in the coil 3, causing a peak detector 24 to detect the maximum value of the output, causing a sample hold circuit 25 to hold the control input of the voltage control oscillation circuit 22, and causing what has been held therein to be output through a low-pass filter 26. In this case, the changing ratio of the resonance frequency fm relative to the variation of the permittivity $\epsilon$ becomes higher because no parallel capacities Cp, Cpa contribute to Cf as shown in Eq. (2) or shown by the equivalent circuit of 5A, 5B. Moreover, the geometrical capacity precision of Cf, Cs can be raised and the variation of the output of the sensor can also be reduced by increasing the dimensional precision of the case 2 and the columnar electrode 6.

FIG. 3 is a graph showing the output characteristics of this sensor and those of a conventional sensor in comparison, the latter having dimensions similar to those of the former in which L=30 $\mu$H, the outer diameter $\phi$ of the thin wall portion 2a of the case 2=10 mm, the thickness t of the thin wall portion 2a=1 mm, and the width d of the fuel channel 4 between the inner periphery of the thin wall portion 2a and the outer periphery of the columnar electrode 6=2 mm. The variation of the resonance frequency fm in the case of fuel as a mixture of gasoline of $\epsilon$=2 and methanol of $\epsilon$=33 amounts to over 20% and this proves the fact that the range of variations has been improved far greater than before.

Embodiment 2

Figure 6:
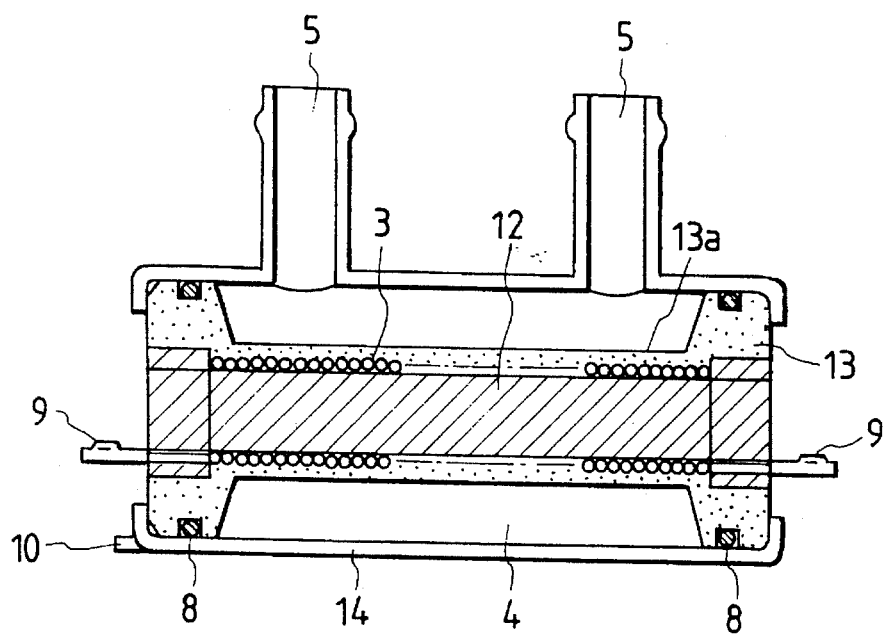
FIG. 6 is a sectional view of a sensor unit in a second embodiment of the present invention.

FIG. 6 is a sectional view of a sensor in a second embodiment of the present invention, the sensor comprising a coil bobbin 12, a coil mold 13 in which a coil 3 is integrally held so that a wound-coil portion forms a thin wall portion 13a, and a cylindrical case electrode 14 simultaneously usable as a case. The coil mold 13 is formed by winding the single-layer coil 3 on the outer periphery of the cylindrical or coaxial coil bobbin 12, then soldering both ends of the coil 3 to a pair of respective coil terminals 9 secured to the coil bobbin 12 by insert molding and further covering the combination above with plastic by injection molding. PPS resin and the like are suitable for use as molding materials.

As the coil bobbin 12 is designed to not come in contact with fuel, plastic material resistant to fuel is not necessarily used for it; however, the use of such plastic material is preferred as heat deformation is avoided when the coil bobbin 12 and the coil mold 13 are made of the same material. The coil mold 13 excluding the thin wall portion 13a is formed in such a way that while the diameter of its both ends substantially corresponds with the inner diameter of the cylindrical case electrode 14, a pair of O-rings 8 are respectively secured to these ends to seal fuel, both ends of the cylindrical case electrode 14 being bent to caulk the respective ends of the mold.

The fuel channel 4 is formed between the inner periphery of the cylindrical case electrode 14 and the outer periphery of the coil mold 13 and there are provided the pair of fuel ports 5 respectively coupled to both end portions by soldering and used to distribute the fuel. Unlike the cylindrical container case 2 of FIG. 4, it is unnecessary for only the thin wall portion 13a to bear the fuel pressure in the embodiment 2. As a result, the thin wall portion 13a can be made thinner and the capacity Cs of the thin wall portion 13a connected to the capacity Cf in series can be increased. In this way, the variation of the permittivity of the fuel relative to the variation of the resonance frequency can be increased further.

Figure 7A:
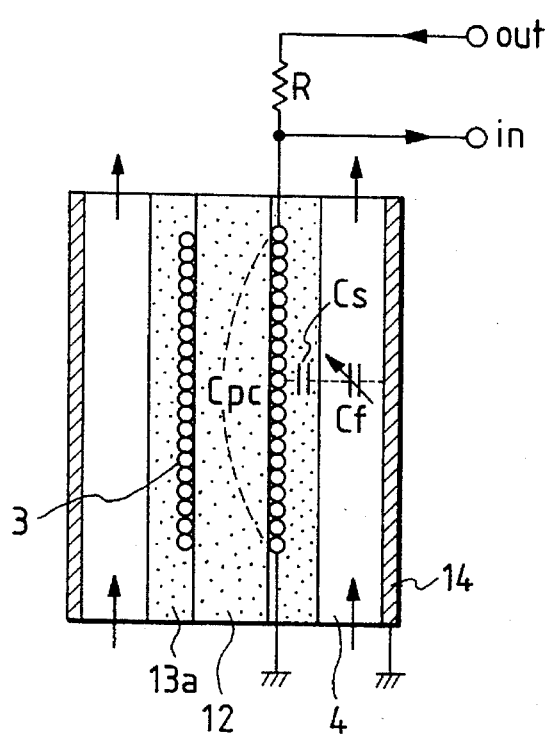
FIGS. 7A and 7B are a block diagram of an equivalent circuit of the sensor unit and an equivalent circuit diagram in the second embodiment of the present invention.
Figure 7B:
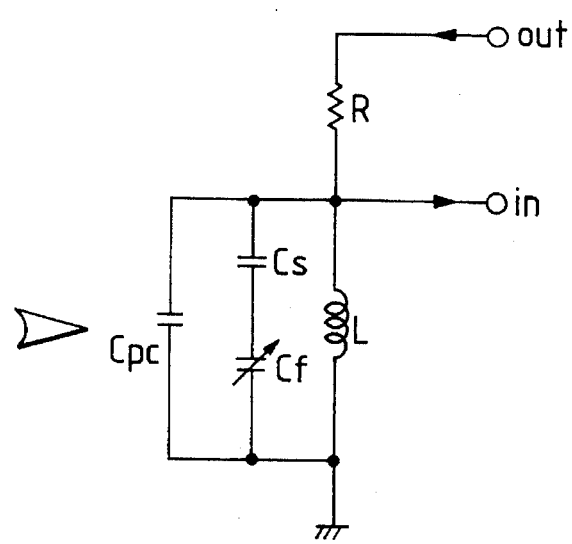

FIGS. 7A, 7B show an equivalent circuit of the sensor unit wherein the cylindrical case electrode 14 and one of the coil terminals 9 are grounded, wherein the output of the voltage control oscillation circuit 22 in the detection circuit B is applied via a resistor R to the other coil terminal 9 and wherein the voltage at the connection between the coil 3 and the resistor R is applied to the full-wave rectifying circuit 23. In this case, the sensor unit forms a parallel resonance circuit whose resonance frequency fn is given by $$fn=1/[2\pi \sqrt{L} \sqrt{\{Cf/(1+Cf/Cs)+Cpc\}}] \quad (3)$$

and the resonance frequency fn also decreases as the permittivity $\epsilon$ of the fuel increases.

The impedance of an LC resonance circuit is maximized at the resonance frequency fn and the voltage at the connection between the coil 3 and the resistor R is also maximized. Accordingly, the voltage output Vout is made to correspond in value to the resonance frequency, that is, the permittivity $\epsilon$ of the fuel through the steps of causing the voltage control oscillation circuit 22 to vary the frequency to be applied via the resistor R to the coil 3, causing the full-wave rectifying circuit 23 to rectify the voltage at the connection between the coil 3 and the resistor R so as to detect the maximum value of the output in the peak detector 24, causing the sample hold circuit 25 to hold the then control input of the voltage control oscillation circuit 22, and causing what has been held therein to be output through the low-pass filter 26.

In Eq. (3), the parallel capacity Cpc of the coil 3 can be made smaller than the capacity Cf and since the coil 3 is in the form of a mold, it remains externally unaffected by moisture, for instance. Since the coil 3 is covered with the cylindrical case electrode 14 thus grounded, moreover, the use of magnetic material such as iron with fuel resistance secured by plating the inner surface of the cylindrical case electrode 14 with nickel can make the coil 3 free from being affected by the external magnetic field. In the embodiment 2, it is possible not only to secure a wide range of resonance frequency variations relative to the variation of permittivity $\epsilon$ of fuel but also to make the sensor output completely free from the external environment.

Embodiment 3

Figure 8:
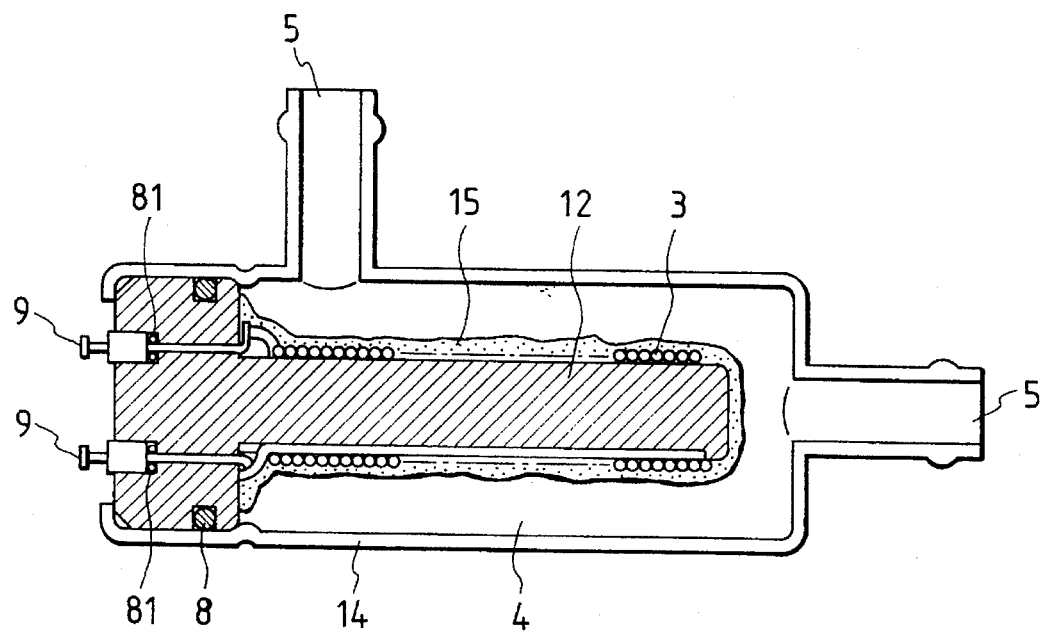
FIG. 8 is a sectional view of a sensor unit in a third embodiment of the present invention.

FIG. 8 is a sectional view of a sensor unit in a third embodiment. Numeral 15 denotes a coating member. A pair of coil terminals 9 are fitted by insert molding into a coil bobbin 12 via O-rings 81 for sealing fuel. A coil 3 is wound on the outer periphery of the coil bobbin 12 and coated by dipping with the coating member 15 after both ends of it are soldered to the coil terminals 9. Lastly, the bobbin 12 together with an O-ring 8 is inserted into a cylindrical case electrode 14 and then the end portion of the cylindrical case electrode 14 is bent and tightened by caulking. Oil resistant epoxy resin or PPS resin is used for the coating member 15.

With this arrangement, the thin wall portion can be made thinner as it is formed of the coating member 15 and since a larger capacity Cs is obtainable, the variation of the resonance frequency can be made greater. At the same time, the sensor can be produced less costly because the process of manufacture is simplified.

Although the coil 3 and a columnar electrode 6 or the cylindrical case electrode 14 have been set coaxial in the embodiment shown, they may not necessarily be coaxial as long as the outer periphery of the coil 3 and the inner periphery of the electrode 14 or the inner periphery of the coil 3 and the outer periphery of the electrode 6 are arranged face-to-face but may be substantially axially paralleled. Moreover, the sensor in the embodiment may also be used for the measurement of the permittivity of any liquid, though a reference has been made to a case where the permittivity of fuel is measured.

Embodiment 4

Figure 9A:
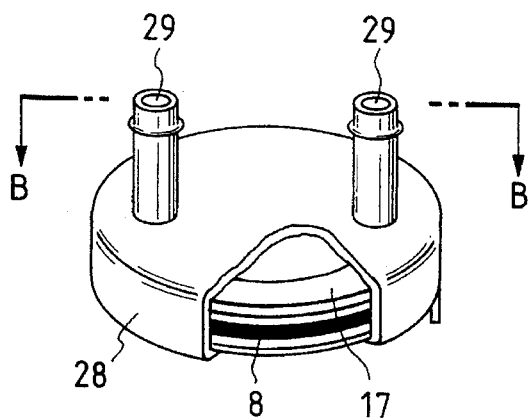
FIGS. 9A and 9B are a perspective and a sectional view of a sensor unit in a forth embodiment of the present invention.
Figure 10A:
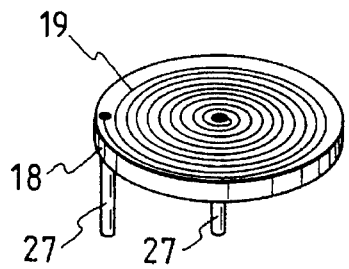
FIGS. 10A and 10B are perspective views of coils in the fourth embodiment of the present invention.
Figure 9B:
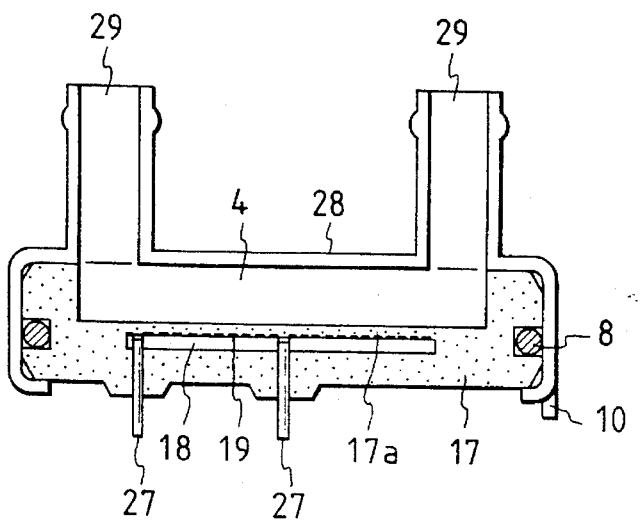
Figure 10B:
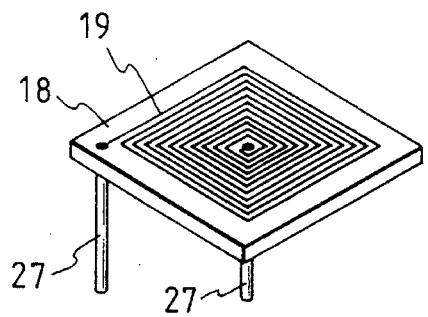

FIG. 9A is a perspective view of a sensor unit in a fourth embodiment and FIG. 9B a sectional view taken on line B—B of FIG. 9A. FIGS. 10A, 10B are perspective views of coil portions. Numeral 17 denotes a disc-like container member formed of plastic insulating material. With respect to the plastic material, oil-resistant epoxy resin, PPS resin and the like having relatively high permittivity are preferred in view of improving the output changing ratio and resistance to fuel. Above all, PPS resin is advantageous as it is fit for injection molding. Numeral 18 is a coil base with a planar single-layer winding coil 19 formed by pattern wiring on its surface; 27, a pair of coil terminals passed through the coil base 18 and connected to the respective ends of the coil 19. The coil base 18, the coil 19 and the coil terminals 27 constitute a coil portion.

As shown in FIG. 10A, the coil portion is prepared by arranging a spiral coil 19 on a circular plate-like plastic laminated base 18 of, for instance, glass epoxy, and soldering the coil terminals 27 via through-holes bored in lead connecting portions at both ends, respectively. A ceramic base may be used for the coil base 18. As shown in FIG. 10B, moreover, a spiral coil 19 may be formed squarely on the square coil base 18. The coil portion is formed by insert molding in the bottom of the disc-like container member 17 with a thin wall portion 17a from the inner bottom surface being left aside.

Numeral 28 denotes a metal case electrode in the form of a cylindrical container arranged a predetermined distance apart from the inner bottom surface of the disc-like container member 17 where the planar single-layer winding coil 19 is provided and also arranged opposite to the planar portion of the bottom, a fuel channel 4 being formed between the surfaces opposite to each other. In view of improving the output changing ratio of the sensor, it is advantageous to set the thickness of the electrode 28 over five times greater than that of the thin wall portion 17a.

A pair of nipples 29 for supplying and discharging fuel to and from the fuel channel 4 are fitted by welding, soldering or the like to the bottom surface of the metal case electrode 28 in such a way as to communicate with the fuel channel 4. The metal case electrode 28 may be made of stainless, titanium or the like; otherwise, it may be made of iron and the inner wall is plated with nickel after the nipples 29 are fitted to secure its resistance to fuel. The disc-like container member 17 has the O-ring 8 arranged on its outer periphery to ensure that fuel is sealed by inserting the O-ring into the cylindrical portion of the metal case electrode 28, both ends of the cylindrical portion being bent and tightened by caulking. Numeral 10 denotes an electrode terminal formed by leaving part of the end portion unbent.

Figure 11A:
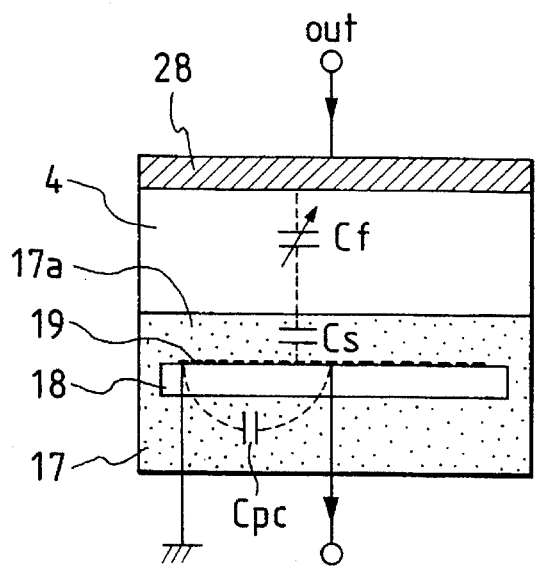
FIGS. 11A and 11B are a block diagram of an equivalent circuit of the sensor unit and an equivalent circuit diagram in the fourth embodiment of the present invention.
Figure 11B:
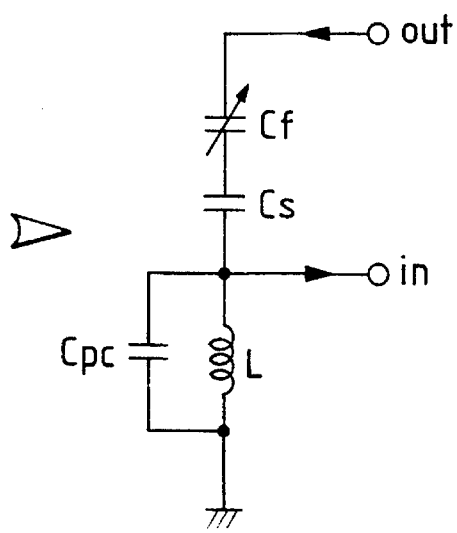

The operation of the sensor in the fourth embodiment will subsequently be described. The detection circuit B of the sensor is similar to what is shown in FIG. 1, wherein the output of a voltage control oscillation circuit 22 is connected to the electrode terminal 10 of the metal case electrode 28 and one coil terminal 27 is grounded, whereas the other coil terminal 27 is connected to a full-wave rectifying circuit 23. In this case, any one of the coil terminals 27 may be grounded. FIGS. 11A and 11B show an equivalent circuit of the sensor unit thus arranged, wherein Cf represents the electrostatic capacity between the bottom surface of the metal case electrode 28 and the wall surface of the thin wall portion 17a at the time fuel having a permittivity $\epsilon$ flows though the fuel channel 4, Cs an electrostatic capacity in the direction of thickness of the thin wall portion 17a, and Cpc a floating capacity existing in parallel to the single-layer winding coil 19. Cf contributes to forming a series resonance circuit with the self-inductance L of the coil 19 and the resonance frequency fm given by Eq. (2) above decreases as the permittivity $\epsilon$ of the fuel increases. Accordingly, the voltage output Vout is made to correspond in value to the resonance frequency fm of the sensor unit, that is, the permittivity $\epsilon$ of the fuel through the steps of causing the voltage control oscillation circuit 22 to vary the frequency to be applied to the metal case electrode 28, causing the full-wave rectifying circuit 23 to rectify the induced voltage in the coil 19 so as to detect the maximum value of the output in the peak detector 24, causing the sample hold circuit 25 to hold the then control input of the voltage control oscillation circuit 22, and causing what has been held therein to be output through a low-pass filter 26.

In this case, the changing ratio of the resonance frequency fm relative to the variation of permittivity $\epsilon$ can be made greater as shown by Eq. (2) or in FIGS. 11A and 11B since no parallel capacities Cp, Cpa contribute to Cf as before. Moreover, the dimensional precision of the face-to-face distance between the bottom surface of the metal case electrode 28 and the thin wall portion 17a and the thickness of the latter can be secured by raising the machining precision of each member. Consequently, the geometrical capacity precision of Cf, Cs can be raised and the variation of the output of the sensor can be reduced. The output characteristics in the fourth embodiment also tend to match the variation shown in FIG. 3 and the variation of the resonance frequency fm in the case of fuel as a mixture of gasoline of $\epsilon=2$ and methanol of $\epsilon=33$ is improved far greater than before.

Figure 12A:
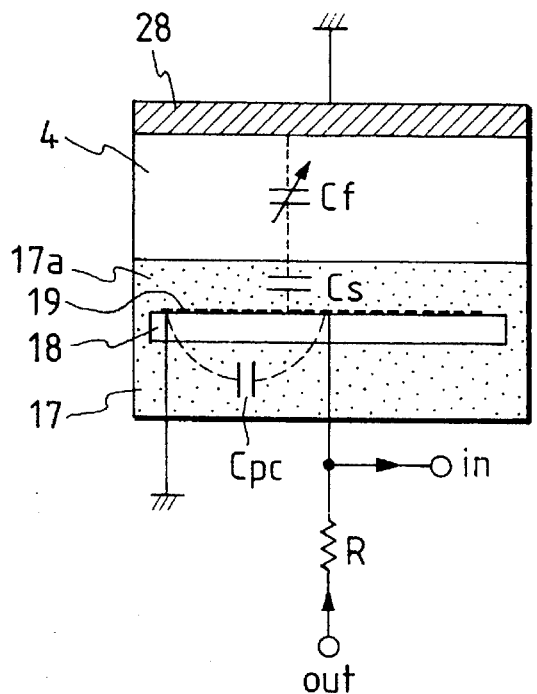
FIGS. 12A and 12B are a block diagram of an equivalent circuit of the sensor unit and an equivalent circuit diagram with the connection of a detection circuit being altered in the fourth embodiment of the present invention.
Figure 12B:
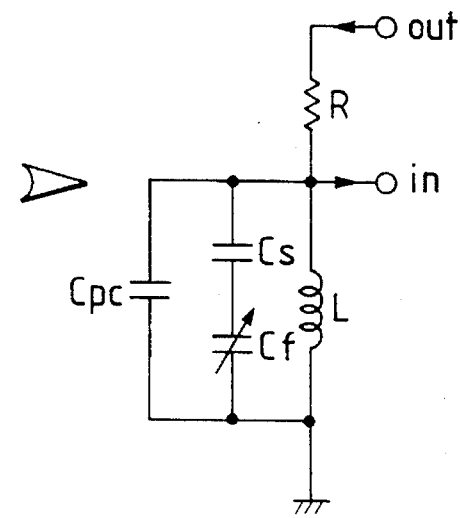

FIGS. 12A, 12B show an equivalent circuit in the sensor unit thus arranged with its connection to a detection circuit being altered. In this case, the metal case electrode 28 and one of the coil terminals 27 are grounded, the other coil terminal 27 being connected via a resistor R to the voltage control oscillation circuit 23, and the coil terminal 27 is connected to the full-wave rectifying circuit 22. The sensor unit forms a parallel resonance circuit and the resonance frequency fn satisfies Eq. (3), whereby the resonance frequency fn decreases as the permittivity $\epsilon$ of fuel increases.

When the frequency levels with the resonance frequency fn, the impedance of the LC parallel resonance circuit is maximized and the voltage at the connection between the coil 19 and the resistor R is also maximized. Accordingly, the voltage output Vout is made to correspond in value to the resonance frequency fn, that is, the permittivity $\epsilon$ of the fuel through the steps of causing the frequency of the signal applied from the voltage control oscillation circuit 22 via the resistor R to the coil 19 to vary, causing the full-wave rectifying circuit 23 to rectify the voltage at the aforementioned connection so as to detect the maximum value of the output in the peak detector 24, causing the sample hold circuit 25 to hold the then control input of the voltage control oscillation circuit 22, and causing what has been held therein to be output through the low-pass filter 26.

In Eq. (3), the parallel capacity Cpc can be made smaller than the capacity Cf as the coil 19 is extremely thin and as the face-to-face area between the coil turns is small. Since the coil 19 is in the form of a mold, it remains externally unaffected by moisture, for instance. Since the coil 19 is covered with the metal case electrode 28 thus grounded, moreover, the use of magnetic material such as iron with fuel resistance secured by plating the inner surface of the metal case electrode 28 with nickel can make the coil 19 less affected by the external magnetic field. In the embodiment 4, it is possible not only to secure a wide range of resonance frequency variations relative to the variation of the permittivity $\epsilon$ of fuel but also to reduce the influence of the external environment on the sensor output.

Embodiment 5

Figure 13:
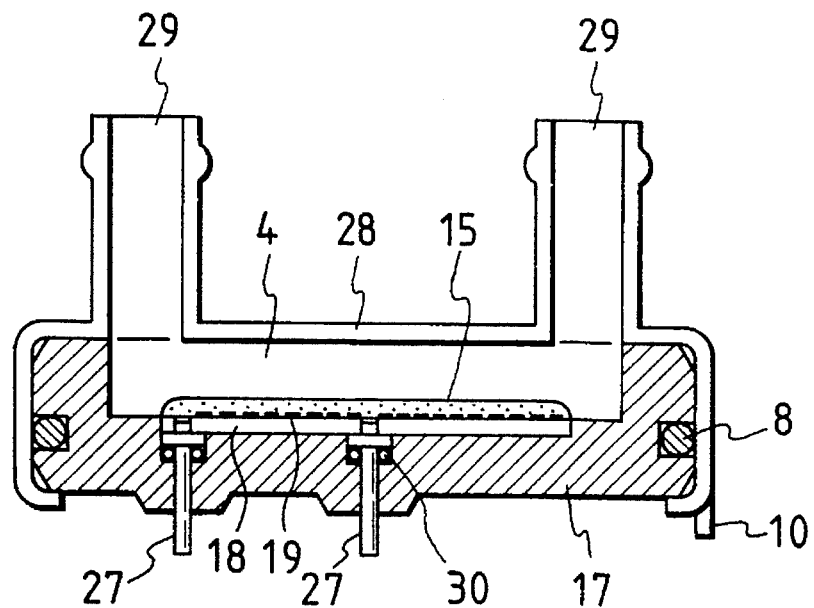
FIG. 13 is a sectional view of a sensor unit in a fifth embodiment of the present invention.

FIG. 13 is a sectional view of a sensor unit in a fifth embodiment. In a coil portion having a coating 15, a planar single-layer winding coil 19 formed by pattern wiring on a coil base 18 and coil terminals 27 connected to the respective ends of the coil 19, the coil 19 is coated by printing or dipping with plastic material which is fuel resistant and has greater permittivity. The coil portion thus arranged is fitted to the bottom surface of a disc-like container member 17 after the coil terminals 27 are inserted into O-rings 30 for sealing fuel. In this case, the coil portion may be fixed by sticking the coil base 18 to a recess in the bottom surface of the disc-like containing member 17 by means of a fuel resistant adhesive or by fusion-caulking around the recess after positioning the coil base 18 at the recess or by simultaneously employing bonding and fusion-caulking. It is not particularly necessary to take into consideration the permittivity of the disc-like container member 17. In this embodiment, the series capacity Cs with respect to Cf can be made greater because the coating 15 can be made thinner than the thin wall portion 17a in the fourth embodiment. As a result, a range of resonance frequency variations relative to the variation of the permittivity of fuel is widened further.

Embodiment 6

Figure 14:
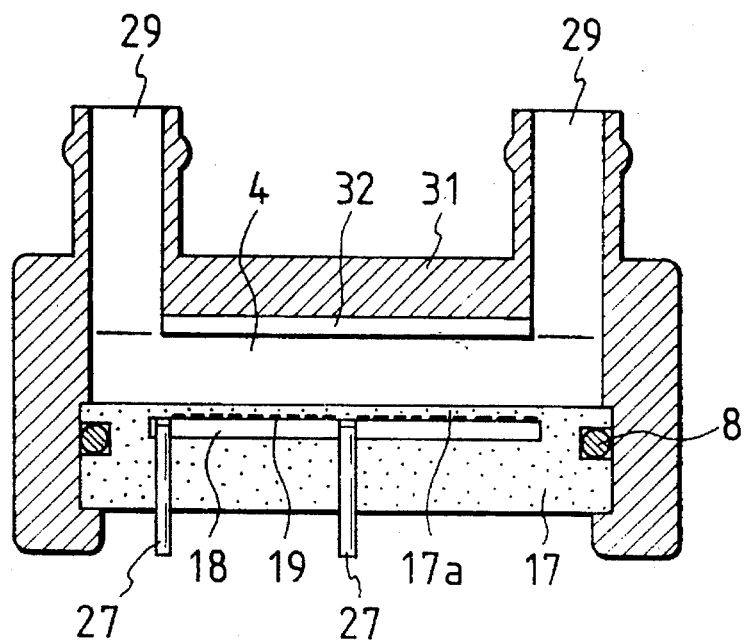
FIG. 14 is a sectional view of a sensor unit in a sixth embodiment of the present invention.

FIG. 14 is a sectional view of a sensor unit in a sixth embodiment. Numeral 31 denotes a cylindrical plastic container case in which a metal electrode plate 32 is formed by insert molding on the bottom surface where nipples 29 are integrally fitted into the cylindrical plastic container case 31. A disc-like container member 17 with a coil portion formed by insert molding is fitted with an O-ring 8 and then inserted into the cylindrical portion of the cylindrical plastic container case 31. The ends of the cylindrical portion is fixed by fusion-caulking or ultrasonic bonding after the disc-like container member 17 is placed in position. The plastic case and the disc-like container member 17 may be made of the same material.

Although the coil 19 has been formed by pattern wiring on the coil base 18 in the embodiments 4–6, any one of substantially planar single-layer winding coils may needless to say serve the purpose. Although a reference has been made to a case where the apparatus is utilized for measurement of the permittivity of fuel, it may also be utilized for measurement of the permittivity of liquids in general.

As set forth above, the fuel channel is formed between the coil and the electrode according to the present invention, and the face-to-face electrostatic capacity between the coil and the electrode is used to detect the permittivity of fuel flowing through the fuel channel. Since the electrostatic capacity is hardly affected by the parallel capacity, a wide range of variations of the electrostatic capacity, which is hardly affected by the parallel capacity, is detected, so that the detecting precision is increased. Moreover, detecting variations can be reduced as the distance between the coil and the electrode is determined with precision.

Embodiment 7

Figure 15:
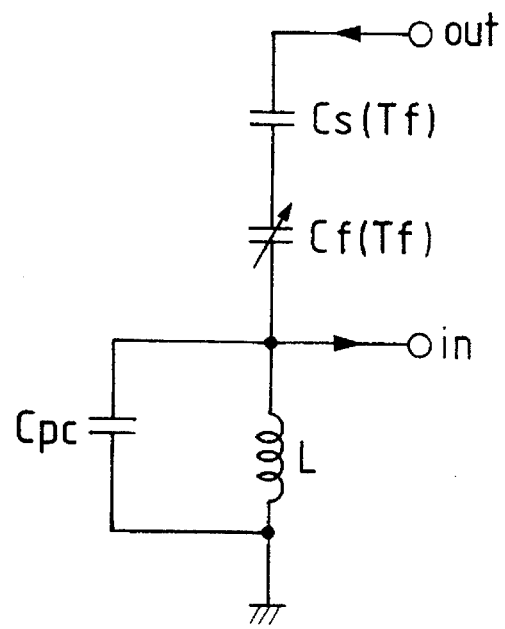
FIG. 15 is an equivalent circuit diagram of the sensor unit of the permittivity detecting apparatus of a seventh embodiment of the present invention.
Figure 16:
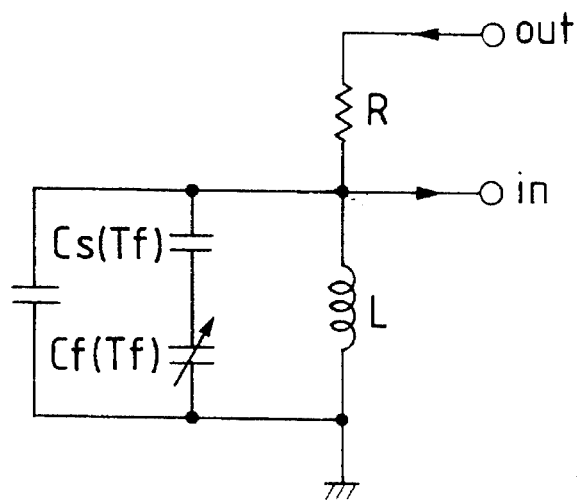
FIG. 16 is en equivalent circuit diagram of the modified sensor unit of FIG. 5.
Figure 17:
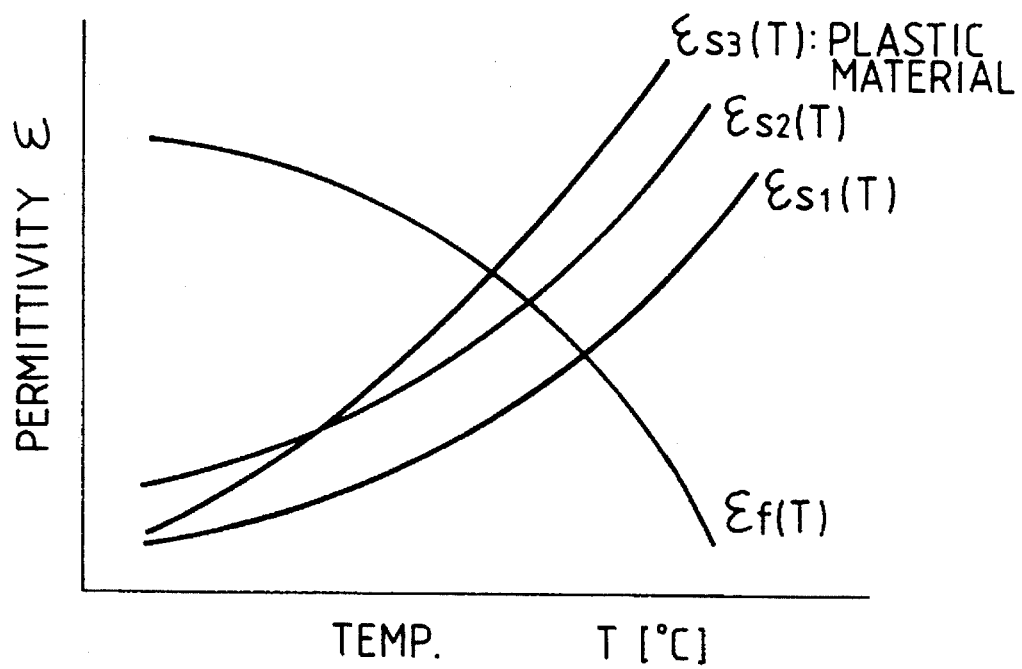
FIG. 17 is a graph showing temperature characteristics of the permittivity of various molding materials.
Figure 18:
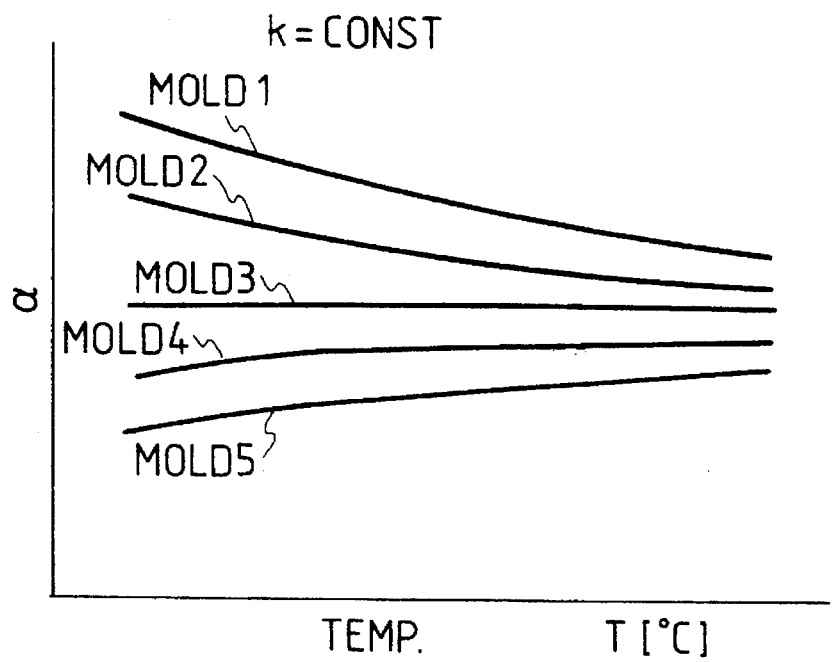
FIG. 18 is a graph illustrating a temperature compensating method with molding materials as those variable in the embodiment shown.
Figure 19:
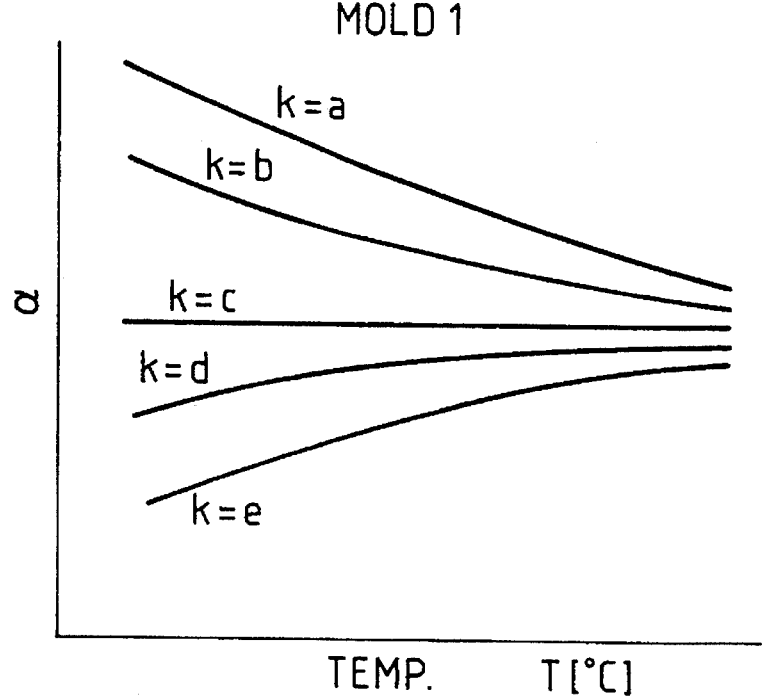
FIG. 19 is a graph illustrating a temperature-compensating method with molding materials as those fixed in the embodiment shown.
Figure 20:
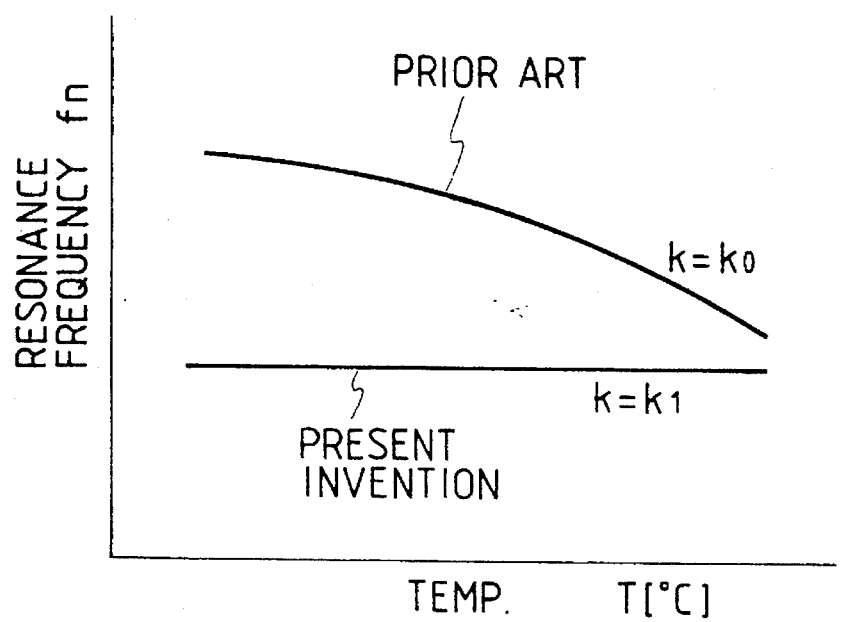
FIG. 20 is a graph showing a comparison of resonance frequencies in the prior art and the present invention wherein temperature compensation is made.

FIGS. 15 and 16 are equivalent circuit diagrams showing temperature dependency of the sensor units of the embodiments 1 to 6. FIG. 17 is a temperature characteristic diagram of permittivity of fuel and plastics of the thin wall portion 2a, 13a, 17a and the coating member 15. FIGS. 18 and 19 are temperature characteristics to explain the temperature compensation of the present invention. FIG. 20 is a comparison diagram of temperature dependency of the output characteristics of the present invention and conventional one.

In the equivalent circuit of FIGS. 15 and 16, an electrostatic capacitance Cf is dependent on the temperature characteristics of the permittivity $\epsilon f$ of the fuel, while an electrostatic capacitance Cs is dependent on the temperature characteristics of the permittivity $\epsilon s$ of the plastic which forms the thin wall portion contacting with fuel, or the coating member. In this case, the permittivity $\epsilon f$ is dependent on the temperature Tf of the fuel, while the permittivity $\epsilon s$ is dependent on the temperature Tf of the fuel since the thin wall portion or the coating member is contacting with the wall. Namely, Cf and Cs are dependent on the temperature Tf of the fuel. A floating capacity Cpc existing in parallel to the coil is also dependent on the temperature because the floating capacity Cpc is determined by the permittivity of the plastic between the coil and the external insulator. However, an influence of the resonance frequency caused by the capacity Cpc is negligible. Therefore, a composite capacity C dependent on the temperature is expressed by the following equation (4).

$$\begin{aligned}
1/C &= 1/Cs + 1/Cf \quad (4)\\
&= 1/\{\epsilon s(Tf) \cdot kK\} + 1/\{\epsilon f(Tf) \cdot K\}\\
&= [1/\{\epsilon s(Tf) \cdot K\} + 1/\{\epsilon f(Tf)\}]/K\\
&= \alpha(Tf)/K
\end{aligned}$$

where kK is a geometrical capacity of Cs; and K is a geometrical capacity of Cf. Therefore, k is a configuration coefficient representing a geometrical capacity ratio of which the capacity Cs is normalized by the capacity Cf.

On condition that the value within [] of Eq. 4 is a constant, the temperature compensation of the apparatus for detecting the permittivity of fuel in the embodiment shown is seen to be accomplished.

As apparent from FIG. 17, the permittivity $\epsilon f$ of fuel decreases with increments in the temperature, alternatively the permittivity $\epsilon s$ of the plastic forming the thin wall portion or the coating member increases with increment of the temperature in a frequency range of from several tens MHz to one hundred and several tens MHz which is an operational frequency band. For this reason, in the case of the series connection of the electrostatic capacities corresponding to their permittivity, the temperature dependency is canceled.

FIG. 18 shows the temperature dependency of the value of $\alpha$ of Eq. (4) in the case of that the configuration coefficient k of the sensor unit shown in FIG. 6 is kept in a constant value and the plastic mold material for forming the thin wall portion 13a is changed. In this case, the mold material is selected from a fuel resistant material such as PPS, Nylon, or Polyamideimide. In FIG. 18, the plastic mold material 3 shows $\alpha$ being no dependency with the temperature. Therefore, the temperature compensation is achieved in the case of the thin wall portion 13a being formed by the plastic mold material 3.

Alternatively, FIG. 19 shows the temperature dependency of the value of $\alpha$ of Eq. (4) in the case of that the configuration coefficient k of the sensor unit shown in FIG. 6 is varied whereas the plastic mold material for forming the thin wall portion 13a is fixed. As apparent from FIG. 19, when the sensor is designed as to be k=c, the temperature compensation is carried out. In the practical application, since the plastic mold material is limited by the reason of durability to the fuel, it is preferable that the temperature compensation is achieved by adjusting the configuration coefficient k of the sensor unit.

FIG. 20 shows the output characteristics of the resonance frequency of the sensor in which the nylon-66 material is used as the molding material and the configuration coefficient k is fixed to a predetermined value, in comparison with those in the conventional art. As apparent form FIG. 20, output according to the present invention has no dependency of the temperature in comparison with that of the conventional example.

As described above, according to the present invention, the temperature characteristics of the permittivity of the fuel is compensated on the basis of the temperature characteristics of the plastic material which forms a thin wall portion contacting with the fuel or a coating member. As a result, the permittivity of fuel is detectable with high accuracy at all times irrespective to the temperature of fuel.

Embodiment 8

Figure 21:
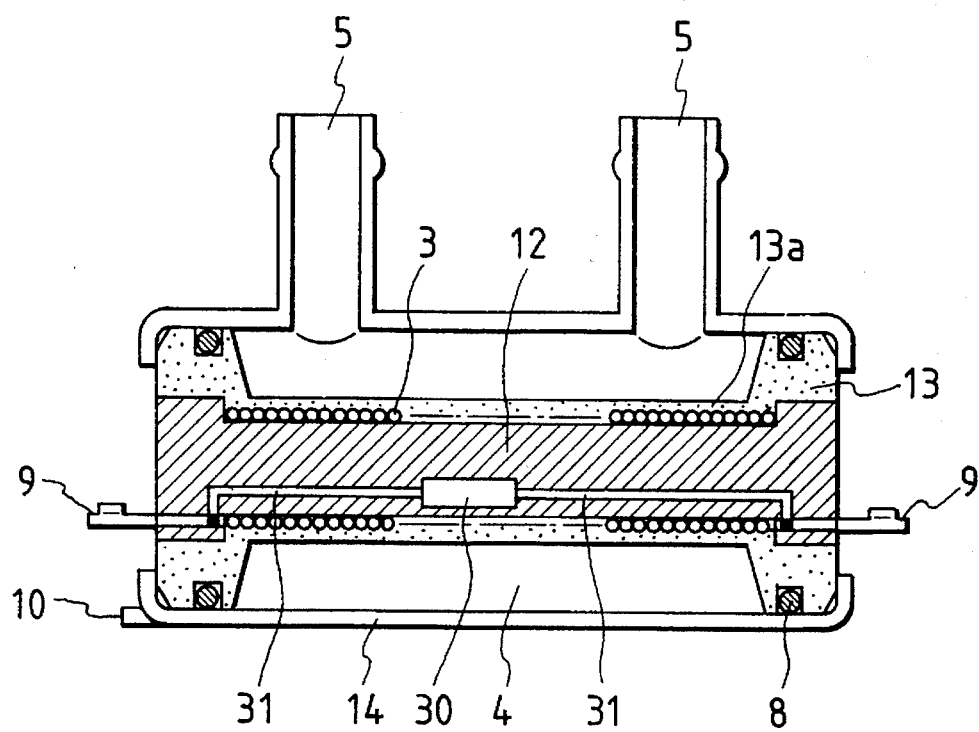
FIG. 21 is a block diagram of an apparatus for detecting the permittivity of fuel in an eighth embodiment of the present invention.

FIG. 21 is a sectional view of the sensor unit according to eighth embodiment of the present invention. The structure is substantially the same as that of FIG. 6. In this embodiment, a temperature compensation capacitor 30 is inserted within the interior of the coil bobbin 12. Leads 31 of both ends of the temperature compensation capacitor 30 are solder-jointed with coil terminals 9 of the coil 3, respectively, to form a parallel circuit.

Figure 22:
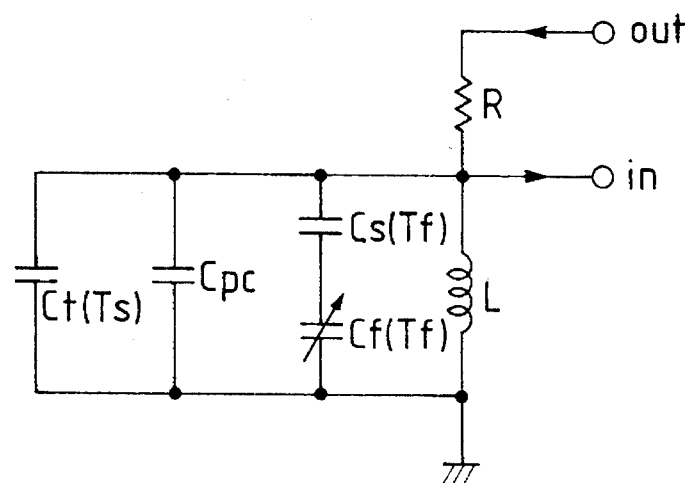
FIG. 22 is an equivalent circuit of the sensor unit in the eighth embodiment of the present invention.

FIG. 22 shows an equivalent circuit of the sensor shown in FIG. 21. As same with FIG. 7, the parallel resonance circuit is formed, and the resonance frequency f is expressed as follow.

$$f = 1/[2\pi\sqrt{L}\sqrt{\{Ct + Cpc + 1/(1/Cs + 1/Cf)\}}] \quad (5)$$

Where Ct is a capacitance of the temperature compensation capacitor 30.

In the equation (5), a serial composite capacitance is same as the equation (4), and is a function with respect to the permittivity $\epsilon f$ of the fuel, the permittivity $\epsilon s$ of the plastic forming the thin wall portion 13a, and the configuration coefficient k. Therefore, as described above, the permittivity εf of the fuel is monotonously decreased with increment of the temperature, whereas the permittivity εs of the plastic is monotonously increased. For this reason, in the case of the series connection of the electrostatic capacities corresponding to their permittivity, the temperature dependency is canceled. The temperature characteristics of the permittivity of the fuel is varied in accordance with the percentage of methanol in the fuel. However, an influence to the temperature characteristic of the output of the sensor by the temperature coefficient of the permittivity of the plastic mold material forming the thin wall portion 13a is larger than that of the permittivity variation according to the methanol percentage.

Figure 23:
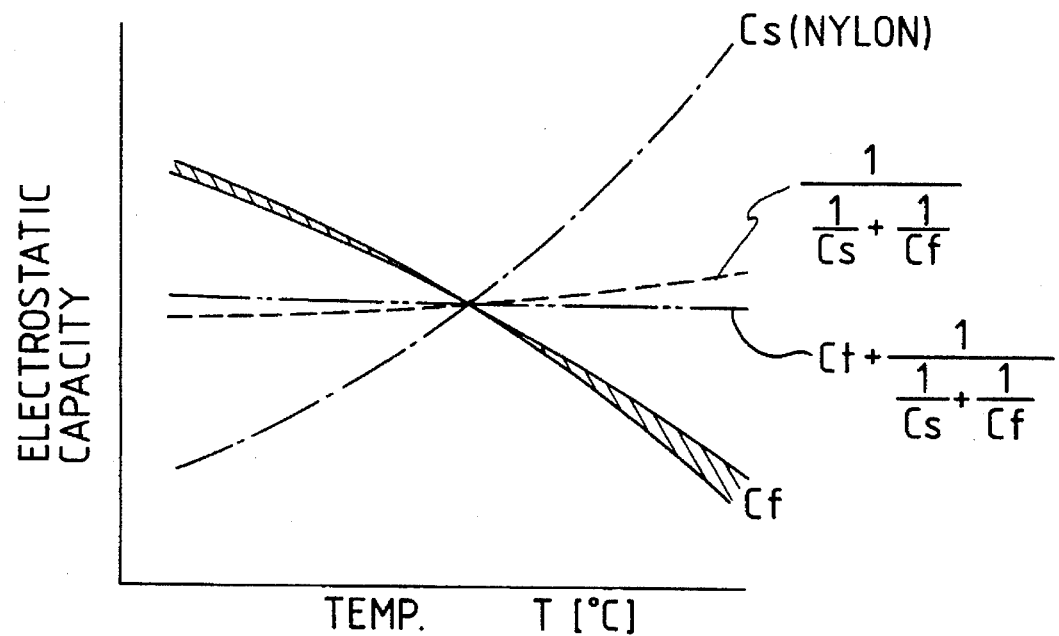
FIG. 23 is a graph showing various electrostatic capacities relative to temperatures.
Figure 24:
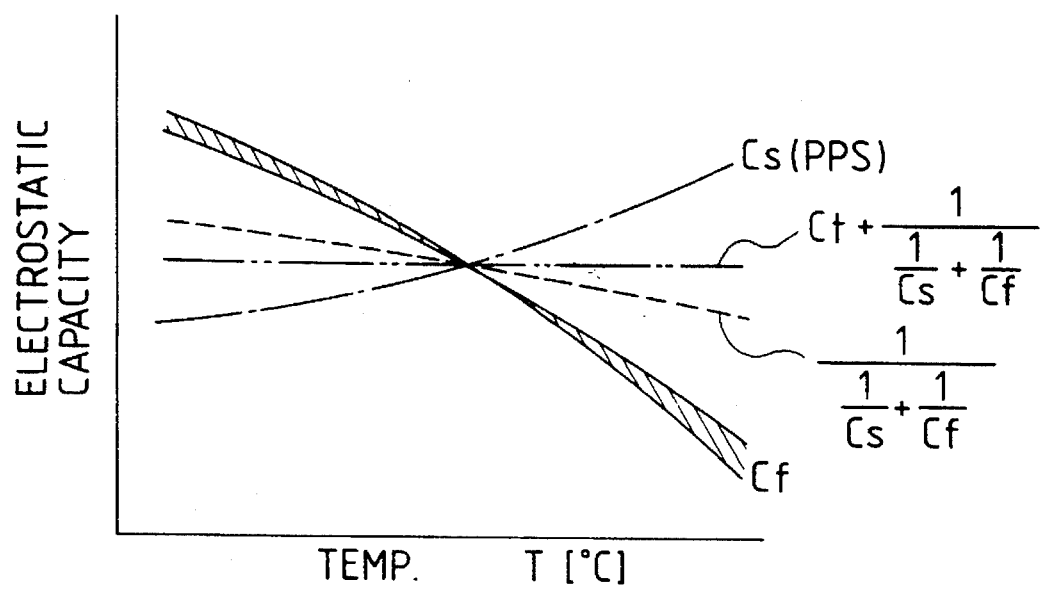
FIG. 24 is a graph showing various electrostatic capacities relative to temperatures.

FIGS. 23 and 24 show the temperature characteristics of the case where the sensor configuration is fixed and the mold material is varied. FIG. 23 shows a case of the nylon is employed as a mold material, whereas FIG. 24 shows a case of PPS is employed. As previously described, the mold material is limited by the reason of the fuel resistance. Therefore, in the case where the temperature compensation capacitor 30 is provided at where the temperature of fuel is detectable, and is connected in parallel with coil 3, the composition capacitance C is given by equation (5).

$$C=Ct(Tf)+Cpc+1/(1/Cs(Tf)+1/Cf(Tf))$$

Figure 25:
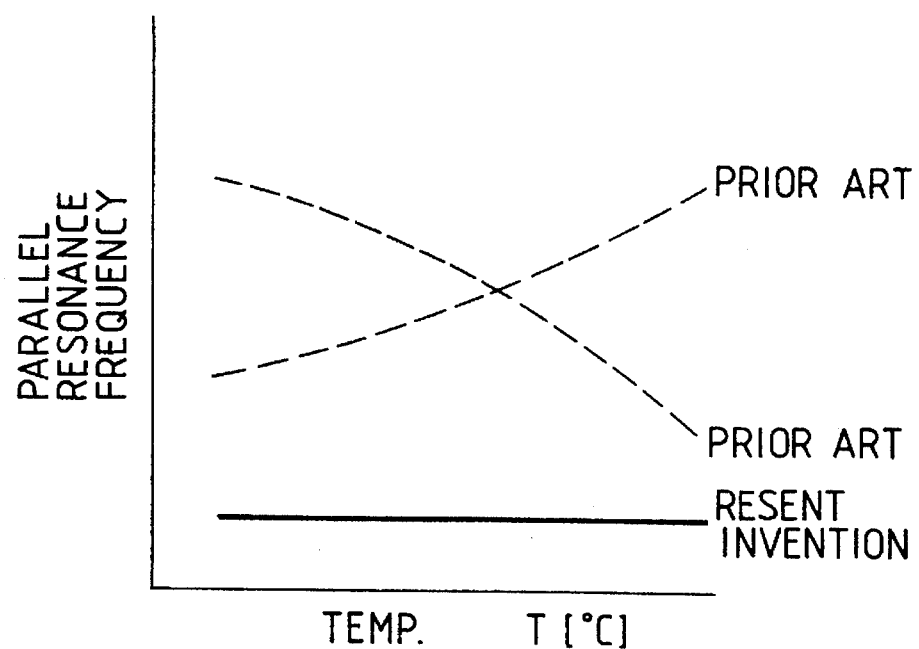
FIG. 25 is a graph showing parallel resonance frequency characteristics relative to temperatures in the prior art and in the embodiment of the present invention.

When a material and a configuration (geometrical capacitance) of the sensor is fixed, a capacitance of the temperature compensation capacitor 30 and a temperature coefficient are determined so that the composite capacitance C is not dependent on the fuel temperature Tf. In FIG. 25, a compensated result of the temperature characteristic of the resonance frequency is shown in comparison with that of conventional art. As apparent form the figure, the temperature characteristic of the output of the sensor is compensated by parallel connection of the temperature compensation capacitor and the coil 3.

Figure 26:
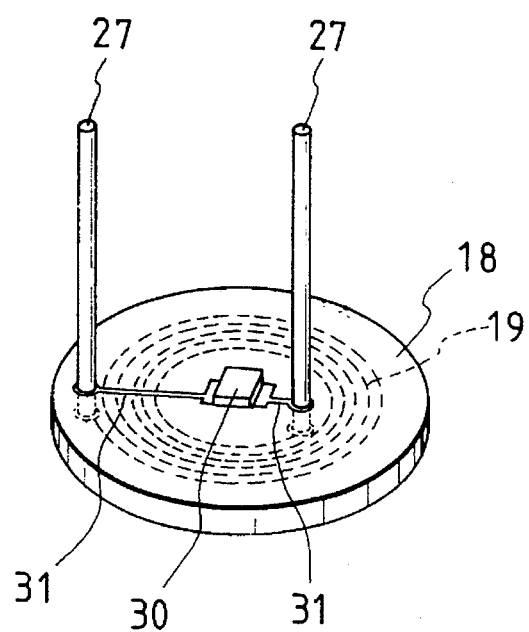
FIG. 26 is a perspective view of a coil of another permittivity detecting apparatus of the present invention.

FIG. 26 is a perspective view of a coil portion in the case of the temperature compensation capacitor 30 being provided on the sensor unit as shown in FIG. 9. In this coil portion, a circular spiral coil 19 is disposed on a surface of a laminated substrate 18 made of a glass epoxy in a form of a circular plate, while the temperature compensation capacitor 30 in the form of a chip is disposed on another surface of the laminated substrate. Lead patterns 31 of the capacitor 30 are connected with lands of lead of the coil 19 so that the temperature compensation capacitor 30 and the coil 19 are connected in parallel with each other. The coil portion is formed by insert molding in the bottom of the disk-like container member 17 with a thin wall portion 17a from the inner bottom surface being left aside as same as the embodiment of FIG. 9. According to this embodiment, the temperature characteristic of the temperature compensation capacitor 30 is dependent on the temperature of the fuel. Therefore, the temperature compensation is achieved as same as the previously described embodiments.

According to the present invention, the single-layer winding coil and the temperature-compensating capacitor are connected in parallel to compensate for the resonance frequency due to the variation of the temperature of fuel as set forth above. Therefore, the alcohol content can be made detectable efficiently and accurately at all times.

What is claimed is:

1. An apparatus for detecting a permittivity of fuel, said apparatus comprising:

single-layer winding coil means provided with a thin insulating layer having high-permittivity, said thin insulating layer being in contact with the fuel;

metal electrode means, disposed concentrically with said single-layer winding coil means and separated from said single-layer winding coil means by a predetermined distance, said metal electrode means defining a fuel channel with said thin insulating layer of said single-layer winding coil means; and means for detecting the permittivity of the fuel flowing through said fuel channel based on an electrostatic capacity between said single-layer winding coil means and said metal electrode means;

wherein said single-layer winding coil means is formed in a tubular shape, and said metal electrode means is formed in a columnar shape.

2. An apparatus for detecting a permittivity of fuel, said apparatus comprising:

single-layer winding coil means provided with a thin insulating layer having high-permittivity, said thin insulating layer being in contact with the fuel;

metal electrode means separated from said single-layer winding coil means by a predetermined distance, said metal electrode means defining a fuel channel with said single-layer winding coil means; and means for detecting the permittivity of the fuel flowing through said fuel channel based on an electrostatic capacity between said single-layer winding coil means and said metal electrode means;

wherein said single-layer winding coil means is formed in a disk shape, and said metal electrode means is formed in a disk shape.

3. An apparatus for detecting a permittivity of fuel, said apparatus comprising:

a planar single-layer winding coil means provided with a thin insulating layer having high-permittivity, said thin insulating layer being in contact with the fuel;

metal electrode means separated from said planar single-layer winding coil means by a predetermined distance, said metal electrode means defining a fuel channel with said planar single-layer winding coil means; and means for detecting the permittivity of the fuel flowing through said fuel channel based on an electrostatic capacity between said planar single-layer winding coil means and said metal electrode means, wherein said detecting means detects said electrostatic capacity between said planar single-layer winding coil means and said metal electrode means, said electrostatic capacity corresponding to said permittivity of the fuel, and wherein temperature characteristics of permittivity of said thin insulating layer compensate for variations of said electrostatic capacity due to temperature characteristics of the permittivity of the fuel.

4. An apparatus for detecting a permittivity of fuel, said apparatus comprising:

a single-layer winding coil means provided with a thin insulating layer having high-permittivity, said thin insulating layer being in contact with the fuel;

metal electrode means separated from said single-layer winding coil means by a predetermined distance, said metal electrode means defining a fuel channel with said single-layer winding coil means; and means for detecting the permittivity of the fuel flowing through said fuel channel based on an electrostatic capacity between said single-layer winding coil means and said metal electrode means, wherein said detecting means detects a resonance frequency of said single-layer winding coil means which corresponds to said permittivity of the fuel, and said apparatus further comprising temperature-compensating capacitor means provided at a position where a variation of the temperature of the fuel is detectable, said temperature-compensating capacitor means being connected to said single-layer winding coil in parallel, whereby the temperature characteristics of said resonance frequency are offset by said temperature-compensating capacitor.

5. An apparatus for detecting a permittivity of fuel, said apparatus comprising:

a cylindrical plastic container case;

a planar single-layer winding coil means disposed in said cylindrical plastic container case and provided with a thin insulating layer having high-permittivity, said thin insulating layer being in contact with the fuel;

metal electrode plate disposed in said cylindrical plastic container case and separated from said planar single-layer winding coil means by a predetermined distance, said metal electrode plate defining a fuel channel with said planar single-layer winding coil means; and means for detecting the permittivity of the fuel flowing through said fuel channel based on an electrostatic capacity between said planar single-layer winding coil means and said metal electrode plate, wherein said detecting means detects said electrostatic capacity between said planar single-layer winding coil means and said metal electrode plate, said electrostatic capacity corresponding to said permittivity of the fuel, and wherein temperature characteristics of permittivity of said thin insulating layer compensate for variations of said electrostatic capacity due to temperature characteristics of the permittivity of the fuel.

6. An apparatus for detecting a permittivity of fuel, said apparatus comprising:

a cylindrical insulating housing having a thin insulating wall, said cylindrical insulating housing having high permittivity;

single-layer winding coil means wound on said thin insulating wall, said thin insulating wall being in contact with said fuel;

metal electrode means, disposed inside of said cylindrical insulating housing and separated from said single-layer winding coil means by a predetermined distance, an outer surface of said metal electrode means defining a fuel channel with an inner surface of said cylindrical insulating housing;

fuel seal means, disposed between said metal electrode means and said cylindrical insulating housing, for sealing said fuel; and means for detecting the permittivity of said fuel flowing through said fuel channel based on an electrostatic capacity between said single-layer winding coil means and said metal electrode means.

7. An apparatus for detecting a permittivity of fuel, said apparatus comprising:

an insulating bobbin arranged as one of a cylindrical insulating bobbin and a coaxial insulating bobbin;

single-layer winding coil means wound on said insulating bobbin, said single-layer winding coil means being coated with an insulating coating material which has a high permittivity, said insulating bobbin having a lead connected to an end of said single-layer winding coil means;

cylindrical metal housing means concentrically arranged with said single-layer winding coil means coated by said insulating coating material so as to accommodate said single-layer winding coil means, an inner surface of said cylindrical metal housing means defining a fuel channel with an outer surface of said single-layer winding coil means coated by said insulating coating material;

first fuel seal means provided between said lead and said insulating bobbin;

second fuel seal means, disposed between said insulating bobbin and said cylindrical metal housing means, for sealing said fuel; and means for detecting the permittivity of said fuel flowing through said fuel channel based on an electrostatic capacity between said single-layer winding coil means and said cylindrical metal housing means.

8. An apparatus for detecting a permittivity of fuel as set forth in claim 7, wherein said detecting means detects a resonance frequency of said single-layer winding coil means which corresponds to said permittivity of the fuel, and said apparatus further comprising a temperature-compensating capacitor means provided at a position where a variation of the temperature of the fuel is detectable, said temperature-compensating capacitor means being connected to said single-layer winding coil means in parallel, whereby the temperature characteristics of said resonance frequency are offset by said temperature-compensating capacitor.

9. An apparatus for detecting a permittivity of fuel, said apparatus comprising:

planar single-layer winding coil means formed on an insulating substrate, said insulating substrate having a lead connected to an end of said planar single-layer winding coil means;

disk shaped insulating molding including a thin wall portion which covers said planar single-layer winding coil means, said disk shaped insulating molding having high permittivity;

metal electrode means, separated from said planar single-layer winding coil means by a predetermined distance, said metal electrode means defining a fuel channel with said disk shaped insulating molding;

fuel seal means, disposed between said disk shaped insulating molding and said metal electrode means, for sealing said fuel; and means for detecting the permittivity of said fuel flowing through said fuel channel based on an electrostatic capacity between said planar single-layer winding coil means and said metal electrode means.

10. An apparatus for detecting a permittivity of fuel, said apparatus comprising:

planar single-layer winding coil means formed on an insulating substrate, said insulating substrate having a lead connected to an end of said planar single-layer winding coil means;

a disk shaped insulating molding for fixing said insulating substrate;

first fuel seal means provided between said lead and said disk shaped insulating molding;

an insulating coating for covering said planar single-layer winding coil means, said insulating coating having high permittivity;

metal electrode means, separated from said planar single-layer winding coil means by a predetermined distance, said metal electrode means defining a fuel channel with said planar single-layer winding coil means covered by said insulating coating;

second fuel seal means, disposed between said disk shaped insulating molding and said metal electrode means, for sealing said fuel; and means for detecting the permittivity of said fuel flowing through said fuel channel based on an electrostatic capacity between said planar single-layer winding coil means and said metal electrode means.

* * * * *